(12) United States Patent
Chamberlain

(10) Patent No.: US 8,751,252 B2
(45) Date of Patent: Jun. 10, 2014

(54) SYSTEMS AND METHODS FOR CLINICAL DATA VALIDATION

(75) Inventor: Forrest Lee Chamberlain, South Burlington, VT (US)

(73) Assignee: General Electric Company, Schenectady, NY (US)

( * ) Notice: Subject to any disclaimer, the term of this patent is extended or adjusted under 35 U.S.C. 154(b) by 956 days.

(21) Appl. No.: 11/741,427

(22) Filed: Apr. 27, 2007

(65) Prior Publication Data

US 2008/0270177 A1    Oct. 30, 2008

(51) Int. Cl.
    *G06Q 50/00* (2012.01)
(52) U.S. Cl.
    USPC .................................... 705/2; 705/3
(58) Field of Classification Search
    USPC ........................................ 705/2–3
    See application file for complete search history.

(56) References Cited

U.S. PATENT DOCUMENTS

| | | | |
|---|---|---|---|
| 5,508,912 A * | 4/1996 | Schneiderman .................. | 705/3 |
| 5,835,758 A * | 11/1998 | Nochur et al. ........................ | 1/1 |
| 6,542,905 B1 * | 4/2003 | Fogel et al. ................... | 707/200 |
| 6,781,607 B1 * | 8/2004 | Benham ........................ | 715/744 |
| 6,876,780 B1 * | 4/2005 | Nielsen et al. ................ | 382/312 |
| 7,043,437 B1 * | 5/2006 | Nielsen et al. ............. | 704/270.1 |
| 7,233,938 B2 * | 6/2007 | Carus et al. ........................ | 707/1 |
| 7,860,287 B2 * | 12/2010 | Zahlmann et al. ............ | 382/128 |
| 2003/0009295 A1 * | 1/2003 | Markowitz et al. ............. | 702/20 |

FOREIGN PATENT DOCUMENTS

| EP | 1868124 A2 | 12/2007 |
|---|---|---|
| WO | 01/55949 A1 | 8/2001 |

OTHER PUBLICATIONS http://www.identityblog.com/stories/2005/07/05/IdentityMetasystem.htm.
http://www.hl7.org/special/Committees/ccow_sigvi.htm.
http://www.hl7.org/library/committees/sigvi/CCOW_overview_2001.doc.
http://medical.nema.org/dicom/spie2002/Security_by_Lawrence_Tarbox.ppt.
Carus, US Patent #7233938, Jun. 19, 2007.
Benham, US Patent #6781607, Aug. 24, 2004.
Great Britain Examination Report for GB0807167.2; May 4, 2011 (7 pages).

* cited by examiner

*Primary Examiner* — Sind Phongsvirajati
(74) *Attorney, Agent, or Firm* — Hanley, Flight & Zimmerman, LLC

(57) ABSTRACT

Certain embodiments of the present invention provide a method for validating clinical data including receiving a consistency requirement, receiving a data claim associated with clinical data, and evaluating the data claim based at least in part on the consistency requirement. Certain embodiments of the present invention provide a clinical data validation system including a consistency requirement input component adapted to receive a consistency requirement, a data claim input component adapted to receive a data claim, and a validation component adapted to evaluate the data claim based at least in part on the consistency requirement. The data claim is associated with clinical data.

19 Claims, 3 Drawing Sheets

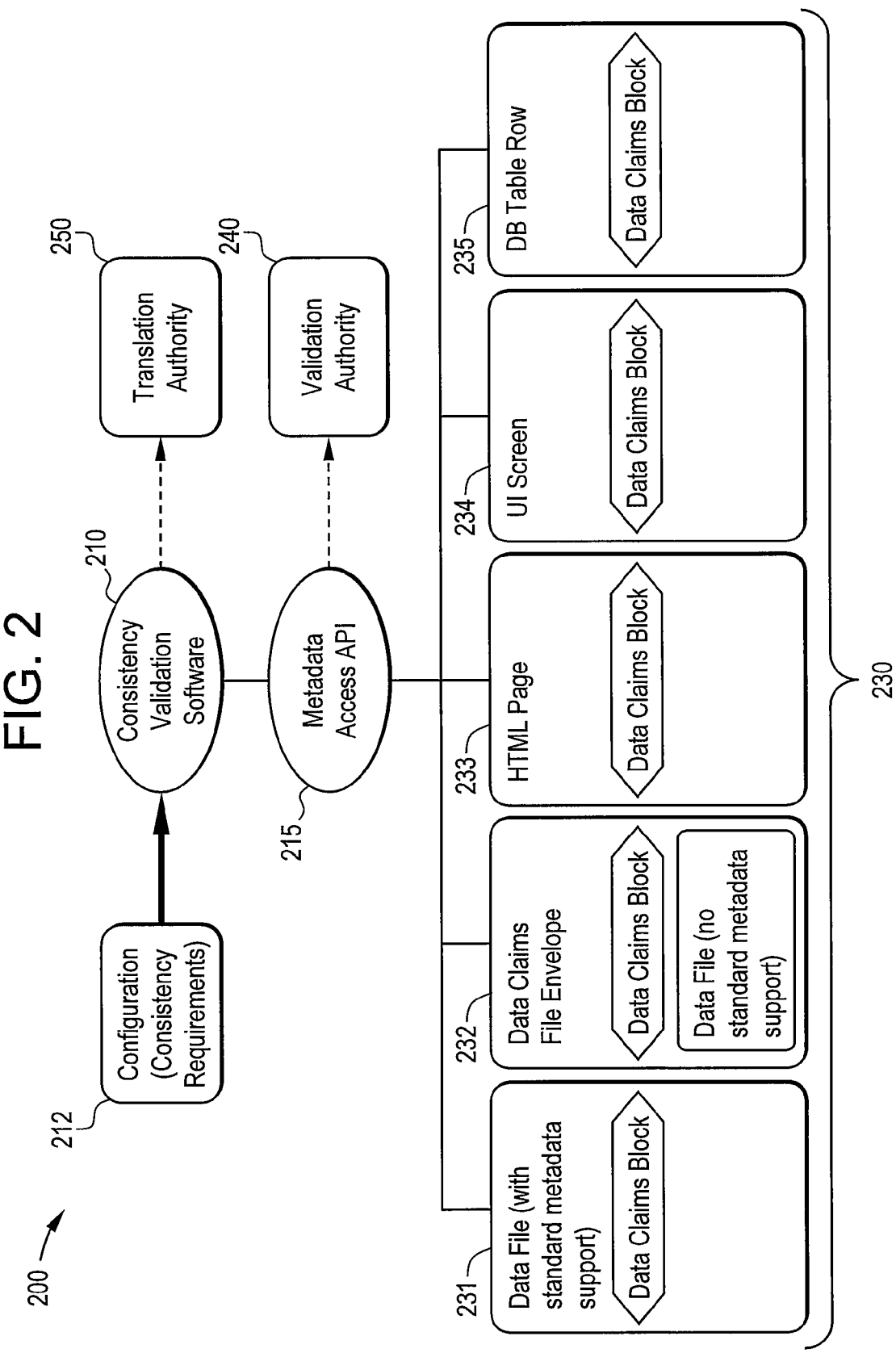

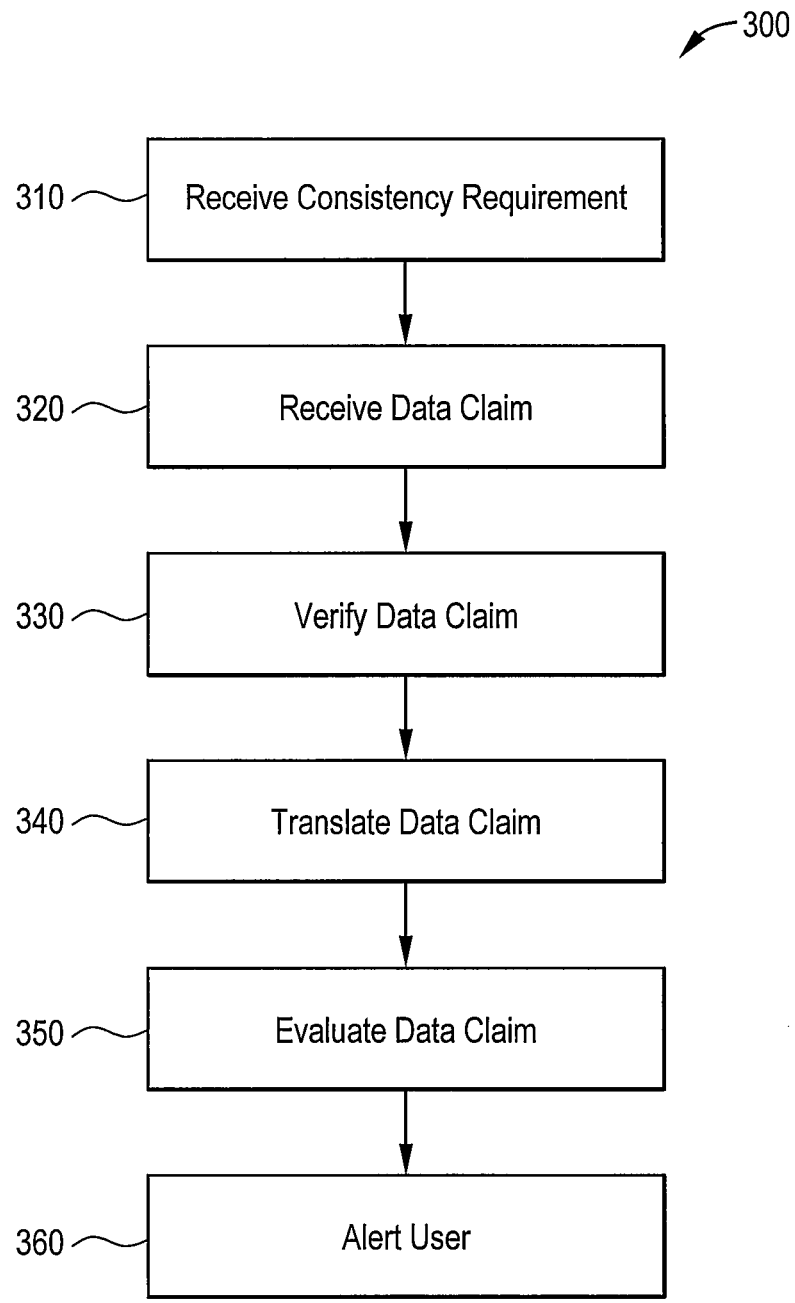

SYSTEMS AND METHODS FOR CLINICAL DATA VALIDATION

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to clinical information systems. More specifically, the present invention relates to systems and methods for clinical data validation.

Healthcare practitioners work with many forms of clinical data, such as images and measurement data from various scanners and modalities and electronic medical records (EMR). The clinical data may be stored in a number of formats. These formats may include a variety of file formats such as Digital Imaging and Communications in Medicine (DICOM) images, Joint Photographic Experts Group (JPEG) images, WAV audio files, and Portable Document Format (PDF) files; Extensible Markup Language (XML) data; and database tables, for example.

Generally, metadata is associated with core clinical data such as an image. The metadata may include, for example, patient identification, exam (accession) number, and time and place of scan. In some cases, metadata is stored as part of the same file as the core clinical data. For example, the DICOM format supports storing metadata in a clinical data file with the image information. However, in many formats, metadata is stored separately from the clinical data itself. For example, a non-DICOM image, such as a JPEG image may have metadata stored in a database. As another example, a WAV audio file containing a dictated report may have metadata stored in a database or XML file. This can lead to the core clinical data and the metadata becoming separated. As a result, there are risks ranging from the loss of the ability to use the clinical data to misidentification of data and ensuing misdiagnosis.

In addition to these risks, there is no standard mechanism for storing or validating the original source, or even the namespace, for any given piece of metadata. For example, different applications and/or systems may use different Medical Record Numbers (MRNs) to identify the same patient. An MRN may be specific to a particular system or care provider, for example.

As mentioned, medical professionals work with many kinds of clinical data. Often, a healthcare provider may view a variety of clinical data for a patient or an exam at one time. For example, a physician may review images acquired by an imaging modality along side a patient's EMR. Some applications make an effort to ensure that they only show consistent data at any one time. That is, an application may attempt to verify that the data displayed to a user is all associated with the current patient or exam. However, this requires explicit coding in each application and is error-prone.

In addition to consistency problems within a single application, consistency across multiple applications is even more problematic. Often, applications that display clinical data are provided by different vendors and thus must cooperate to try to ensure consistency.

Health Level 7 (HL7) provides a standard called Clinical Context Object Workgroup (CCOW). The CCOW standard provides for an architecture that attempts to ensure consistency across different data elements. A CCOW-compliant application communicates with a context manager to set a patient context. For example, the CCOW-compliant application may identify the MRN of the current patient. The context manager then notifies other CCOW-compliant applications of the current context. These applications, in turn, should update their internal state and display data accordingly. However, CCOW does not guarantee that the applications have done so. In addition, CCOW does not address the problem of a single application that has a bug that results in two or more pieces of inconsistent clinical data being presented to a user. Thus, while CCOW facilitates communication between components which display clinical data of the current patient context, CCOW does not validate that displayed clinical data actually complies with the patient context.

The possibility of inconsistency in the presentation of clinical data may cause inefficiencies in development and in clinical workflow, as well as clinical hazards to patients who could be misdiagnosed if an application provides inconsistent clinical data.

Thus, there exists a need for systems and methods for clinical data validation.

BRIEF SUMMARY OF THE INVENTION

Certain embodiments of the present invention provide a method for validating clinical data including receiving a consistency requirement, receiving a data claim associated with clinical data, and evaluating the data claim based at least in part on the consistency requirement.

Certain embodiments of the present invention provide a clinical data validation system including a consistency requirement input component adapted to receive a consistency requirement, a data claim input component adapted to receive a data claim, and a validation component adapted to evaluate the data claim based at least in part on the consistency requirement. The data claim is associated with clinical data.

Certain embodiments of the present invention provide a computer-readable medium including a set of instructions for execution on a computer, the set of instructions including a consistency requirement input routine, a data claim input routine, and a validation input routine. The consistency requirement input routine is configured to receive a consistency requirement. The data claim input routine is configured to receive a data claim. The data claim is associated with clinical data. The validation routine is configured to evaluate the data claim based at least in part on the consistency requirement.

BRIEF DESCRIPTION OF SEVERAL VIEWS OF THE DRAWINGS

FIG. 2 illustrates a system for validating clinical data according to an embodiment of the present invention.

FIG. 3 illustrates a flow diagram for a method for validating clinical data according to an embodiment of the present invention.

Figure 1:
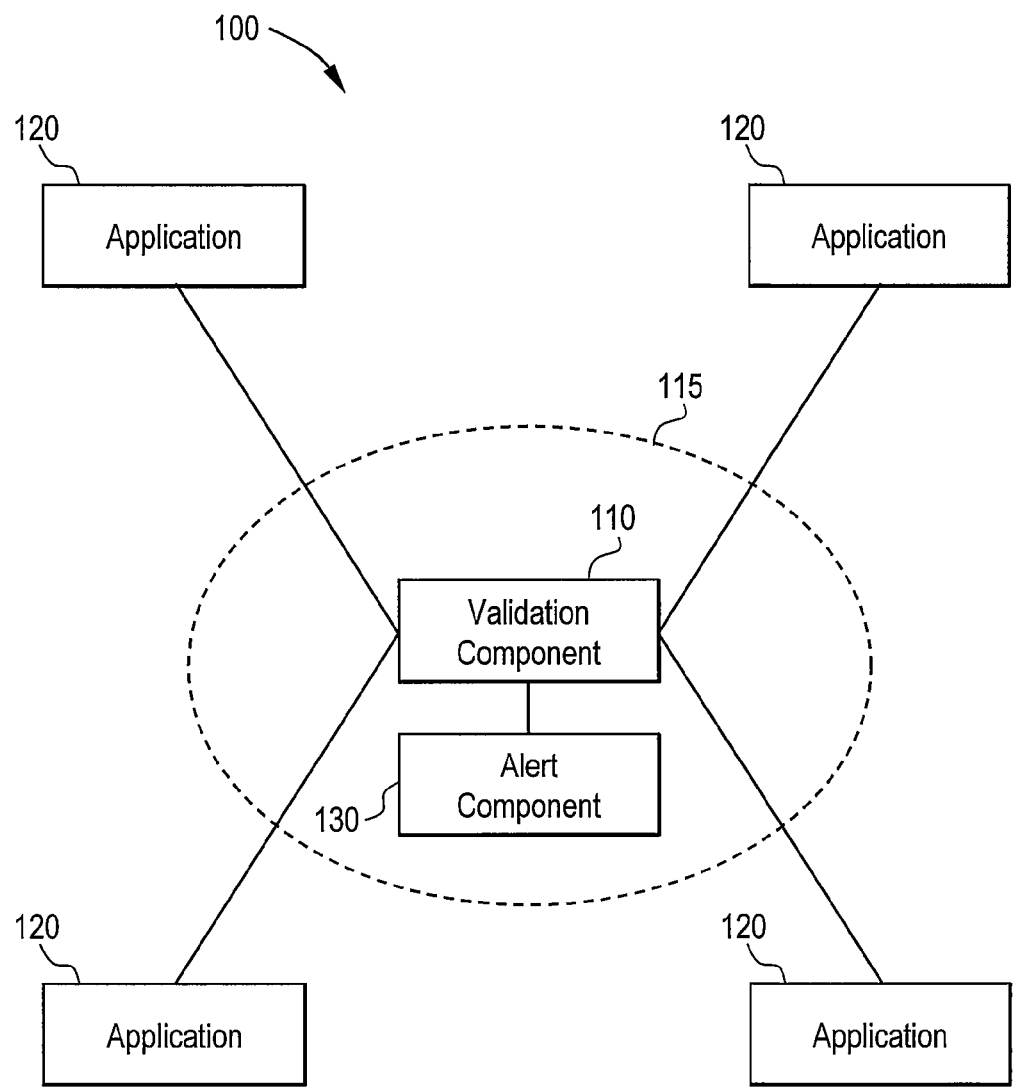
FIG. 1 illustrates a system for validating clinical data according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a system 100 for validating clinical data according to an embodiment of the present invention. The system 100 includes a validation component 110, one or more applications 120, and an alert component 130.

The validation component 110 is in communication with the applications 120. In certain embodiments, the applications 120 and the validation component 110 communicate through an application programming interface (API) 115. The validation component 110 is in communication with the alert component 130.

In operation, a consistency requirement is provided to the validation component 110. The consistency requirement specifies one or more criteria for evaluating the consistency of data claims. Data claims are provided to the validation component 110 from the applications 120. The data claims are associated with clinical data to be presented to a user by the applications 120. The data claims are evaluated by the validation component 110 based at least in part on the consistency requirement. The user is notified by the alert component 130 when the evaluation indicates a violation of the consistency requirement has occurred.

The consistency requirement may be provided by a user, such as a healthcare provider, physician, or nurse, for example. The consistency requirement is received by the validation component 110. The consistency requirement may specify a variety of different conditions to be met. The consistency requirement may include one or more conditions. If the consistency requirement is not met, a violation is said to occur. For example, the consistency requirement may include criteria that clinical data be for the same patient. That is, the consistency requirement is violated when data claims for each piece of clinical data to be presented to the user are determined to not be for the same patient. As another example, the consistency requirement may include a condition that each image be from the same imaging session or exam. That is, the consistency requirement is violated when data claims for each image to be presented to the user are determined to not have been acquired during the same imaging session or exam. As another example, the consistency requirement may require that data from only a defined set of trusted sources is to be displayed. As another example, the consistency requirement may require that only data collected during the past year is to be displayed. As another example, the consistency requirement may require that the data displayed have been collected at a specified hospital.

A data claim is associated with clinical data. The clinical data may be presented to a user. A data claim is metadata that makes "claims" about the associated clinical data. That is, each data claim is treated as an assertion that the value of the claim is correct. For example, a data claim called "creation date" may include a value of "Nov. 14, 2006." This data claim is treated as an assertion that the creation date of the associated clinical data is Nov. 14, 2006. In certain embodiments, a data claim is implemented as a set of (name, value) pairs. The data claims are stored as (name, value) pairs to maximize flexibility, however, other formats may be used.

In certain embodiments, a set of "well-known" fields with predefined names are provided that a compliant system supports. This may allow a base-level of interoperability. For example, these fields may include patient identifiers, exam identifiers, MRNs, creation dates, modification dates, and source of the clinical data. In addition, in certain embodiments, systems may be customized to define their own fields, which will then support interoperation amongst only those applications for those fields.

A set of claims is referred to as a data claims block. A data claims block includes one or more data claims. In addition, the data claims block may include a digital signature. Alternatively, the data claim itself may include a digital signature. The digital signature may be used to verify the data claims and/or the clinical data. In certain embodiments, the digital signature is generated from one or more data claims in the data claims block. In certain embodiments, the digital signature is generated from the data claims and the clinical data. For example, the digital signature may allow a system or user to verify that the data has not been tampered with. As another example, the digital signature may allow a system or user to verify that the metadata came from the specified validation authority using standard cryptographic techniques.

An application 120 provides clinical data to a user. For example, the application 120 may display an image from an acquisition modality or a patient's medical records to a physician. The application communicates data claims associated with the clinical data to be displayed to the validation component 110.

The validation component 110 is adapted to receive a consistency requirement. For example, the validation component 110 may receive a consistency requirement from a user. The consistency requirement may be received by a consistency requirement input component of the validation component 110, for example. That is, in certain embodiments, the validation component 110 includes a consistency requirement input component adapted to receive a consistency requirement.

The validation component 110 is adapted to receive one or more data claims. For example, the validation component 110 may receive a data claim from an application 120. For example, the validation component 110 may receive multiple data claims from a single application 120. As another example, the validation component 110 may receive multiple data claims from different applications 120.

The data claim may be received through the API 115, for example. The data claim may be received by a data claim input component of the validation component 110, for example. That is, in certain embodiments, the validation component 110 includes a data claim input component adapted to receive a data claim.

The validation component 110 is adapted to evaluate data claims associated with clinical data to be displayed to a user by one or more applications 120 using the consistency requirement. When a data claim for clinical data violates the consistency requirement, the user may be alerted. The user may be alerted by the alert component 130, for example.

The alert component 130 is adapted to alert a user when clinical data to be presented violates the consistency requirement. More particularly, if the data claims associated with clinical data are evaluated to violate the consistency requirement, the user is alerted.

The alert component 130 may alert the user in a variety of ways. For example, the alert component 130 may generate an audible or visual alert, such as a beep or a flashing window. As another example, the alert component 130 may generate a pop-up window to signal to a user that inconsistent data is being displayed.

In certain embodiments, the data claims may be communicated from the application 120 to the validation component 110 through the API 115. That is, certain embodiments include a standard API for manipulation and communication of data claims. The API 115 may include calls to interrogate, set, and validate claims for clinical data, for example. The API 115 may provide unified access to clinical data of a variety of types, include those that support data claim metadata within the file format as well as types that do not. The various types of formats of clinical data are discussed in more detail below.

The following is an example of the operation of an embodiment of the present invention. A patient has a computed tomography (CT) scan done at some point in time. The CT scanner, which has been adapted to provide the data claims according to an embodiment of the present invention, includes a data claims block in each image it outputs. This block shows the facility at which the scan was performed as the validation authority, and includes claims about the identity of the patient, an accession number for the exam, the date the exam took place, etc. Later, the same patient has an EKG performed at another hospital. Because the EKG machine has not been adapted to use data claims according to an embodiment of the present invention, an external piece of software then injects a data claims block into the EKG data after it has been generated. At a still later date, the patient visits the emergency room. A clinician looking at the patient's medical history then brings up a variety of clinical data for the patient which are stored on a variety of data systems, including data from the CT scan and EKG performed earlier. In addition, the clinician inadvertently brings up a scan for another patient. Because the clinician had configured her desktop data claims validation system to verify that all displayed data is for a single patient, she is notified that she is viewing inconsistent data. After closing the data for the other patient, the warning clears—the validation system, via the use of a translation authority, establishes that the EKG and the CT Scan, though performed at different facilities, are for the same patient, and hence are in compliance with the user's stated requirements.

FIG. 2 illustrates a system 200 for validating clinical data according to an embodiment of the present invention. The system 200 includes a validation component 210 (e.g., consistency validation software), a metadata application programming interface (API) 215, and clinical data 230. In certain embodiments, the system 200 includes a validation authority 240. In certain embodiments, the system 200 includes a translation authority 250.

The validation component 210 is in communication with the metadata API 215. If present, the validation component 210 is in communication with the validation authority 240. If present, the validation component 210 is in communication with the translation authority 250.

The validation component 210 may be similar to the validation component 110, discussed above, for example. The metadata API 215 may be similar to the API 115, discussed above, for example.

In operation, the validation component 210 receives one or more consistency requirements 212 (e.g., configuration). The consistency requirements 212 specify one or more criteria for evaluating the consistency of data claims. The validation component 210 receives one or more data claims. The data claims are associated with the clinical data 230. The clinical data 230 includes the data claims as metadata. The data claims may be received through the metadata API 215. The clinical data 230 may be used by one or more applications. The validation component 210 evaluates the data claims based at least in part on the consistency requirements 212. A user may be notified when the evaluation indicates a violation of a consistency requirement 212 has occurred.

The consistency requirements 212 may be similar to the consistency requirements discussed above, for example. The consistency requirements 212 may be provided by a user, such as a healthcare provider, physician, or nurse, for example. The consistency requirements 212 may specify a variety of different conditions to be met. The consistency requirement 212 may include one or more conditions. If a consistency requirement 212 is not met, a violation is said to occur. For example, a consistency requirement 212 may include criteria that clinical data be for the same patient. That is, the consistency requirement 212 is violated when data claims for each piece of clinical data to be presented to the user are determined to not be for the same patient.

The clinical data 230 is associated with one or more data claims. The data claims may be similar to the data claims discussed above, for example. A data claim is metadata that makes "claims" about the associated clinical data. That is, each data claim is treated as an assertion that the value of the claim is correct. For example, a data claim called "creation date" may include a value of "Nov. 14, 2006." This data claim is treated as an assertion that the creation date of the associated clinical data is Nov. 14, 2006. In certain embodiments, a data claim is implemented as a set of (name, value) pairs. The data claims are stored as (name, value) pairs to maximize flexibility, however, other formats may be used.

In certain embodiments, a set of "well-known" fields with predefined names are provided that a compliant system supports. This may allow a base-level of interoperability. For example, these fields may include patient identifiers, exam identifiers, MRNs, creation dates, modification dates, and source of the clinical data. In addition, in certain embodiments, systems may be customized to define their own fields, which will then support interoperation amongst only those applications for those fields.

A set of claims is referred to as a data claims block. A data claims block includes one or more data claims. The clinical data 230 may be stored in a number of formats. In some formats, the data claims may be incorporated into the clinical data 230 as metadata. For example, a data file that supports metadata 231 may have a data claims block inserted as metadata. As another example, an XML or HTML page 233 (e.g., a user interface or medical record) may have a data claims block inserted according to a standard format inline with the HTML or XML. As another example, a user interface screen 234 may have a data claims block inserted. As another example, a row 235 of a database table may have a data claims block inserted as another column in the table. The data claims may be represented as a binary large object (BLOB) for the new column entry for the database row 235. As another example, the data claims may be represented as text, which may be encoded, in a separate table referenced by foreign key.

However, some formats of clinical data do not support including the data claims. For example, a data file may not support metadata. Thus, to associate the data claims with the data file, a data claims file envelope 232 is used. The data claims file envelope 232 includes the clinical data, or a reference to the clinical data, along with the data claims. The metadata API 215 is adapted to allow the data claims and the clinical data to be accessed from the data claims file envelope 232. The data claims file envelope 232 may be used on a wide variety of file formats at the cost of having to "wrap" and "unwrap" the data for direct use in an application.

The above described mechanism for incorporating data claims into various formats of clinical data provides a generalized system for storing clinical metadata embedded with the associated clinical data across multiple data storage formats. This mechanism provides for simpler, more reliable maintenance of metadata for clinical data.

The validation component 210 is adapted to receive a consistency requirement 212. For example, the validation component 210 may receive a consistency requirement 212 from a user. The consistency requirement 212 may be received by a consistency requirement input component of the validation component 210, for example. That is, in certain embodiments, the validation component 210 includes a consistency requirement input component adapted to receive a consistency requirement 212.

The validation component 210 is adapted to receive one or more data claims. For example, the validation component 210 may receive a data claim from an application. The application may be similar to the application 120, discussed above, for example. For example, the validation component 210 may receive multiple data claims from a single application. As another example, the validation component 210 may receive multiple data claims from different applications 120.

The data claim may be received through the metadata API 215, for example. The data claim may be received by a data claim input component of the validation component 210, for example. That is, in certain embodiments, the validation component 210 includes a data claim input component adapted to receive a data claim.

The validation component 210 is adapted to evaluate data claims associated with clinical data to be displayed to a user by one or more applications using the consistency requirement 212. When a data claim for clinical data violates the consistency requirement 212, the user may be alerted. The user may be alerted by the alert component, for example. The alert component may be similar to the alert component 130, discussed above, for example.

In certain embodiments of the present invention, the system 200 includes one or more validation authorities 240. A validation authority is an entity, such as software, hardware, an imaging modality, or an organization, that generates a data claim. For example, a CT scanner adapted according to an embodiment of the present invention may be a validation authority 240. When clinical data (e.g., a medical image) is generated by the validation authority 240 (e.g., the CT scanner), one or more data claims are generated and associated with the clinical data by the validation authority 240.

In certain embodiments, the validation authority 240 also generates a digital signature for the data claims and/or the clinical data. The digital signature may be used to verify the data claims, for example. The digital signature may be similar to the digital signature discussed above, for example.

In certain embodiments, the validation authority 240 is adapted to receive and verify the accuracy of data claims in the clinical data 230. For example, the validation component 210 may receive a data claims block for clinical data 230. The validation component 210 may then utilize the validation authority 240 that generated the data claims block (as indicated by a data claim in the data claims block, for example) to verify that the data claims received by the validation component 210 are correct. That is, the validation authority 240 may vouch for the accuracy of the data claims. The validation component 210 may communicate with the validation authority 240 through the metadata API 215, for example.

In certain embodiments, a user may trust one or more validation authorities 240 and not trust other validation authorities 240. For example, the validation component 210 may be configured to utilize only trusted validation authorities 240. The trusted or non-trusted validation authorities 240 may be specified as part of a consistency requirement, for example. When a non-trusted validation authority is needed to validate a data claim, the validation component 210 may provide a warning to the user. The warning may be provided using an alert component similar to the alert component 130, discussed above, for example.

In certain embodiments of the present invention, the system 200 includes one or more translation authorities 250. A translation authority 250 is adapted to translate a data claim from one namespace to another namespace. Data claims generated by different systems (e.g., validation authorities 240), may have different namespaces. For example, different hospitals may use different identifiers to identify the same patient. Thus, even though data claims may logically be for the same patient, the data claims themselves may include different values for the patient identifier because the values are from different namespaces.

The validation component 210 may use a translation authority 250 to translate a data claim from the namespace of one system to the namespace of another system. The validation component 210 may communicate with the translation authority 250 through the metadata API 215, for example.

The components, elements, and/or functionality of system 100 and system 200 may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device.

FIG. 3 illustrates a flow diagram for a method 300 for validating clinical data according to an embodiment of the present invention. The method 300 includes the following steps, which will be described below in more detail. At step 310, a consistency requirement is received. At step 320, a data claim is received. At step 330, a data claim is verified. At step 340, a data claim is translated. At step 350, a data claim is evaluated. At step 360, a user is alerted. The method 300 is described with reference to elements of systems described above, but it should be understood that other implementations are possible.

At step 310, a consistency requirement is received. The consistency requirement specifies one or more criteria for evaluating the consistency of data claims. The consistency requirement may be similar to the consistency requirement 212, discussed above, for example.

The consistency requirement may be provided by a user, such as a healthcare provider, physician, or nurse, for example. The consistency requirement may be received by a validation component, such as the validation component 110 and/or the validation component 210, discussed above, for example. The consistency requirement may specify a variety of different conditions to be met. The consistency requirement may include one or more conditions. If the consistency requirement is not met, a violation is said to occur. For example, the consistency requirement may include criteria that clinical data be for the same patient. That is, the consistency requirement is violated when data claims for each piece of clinical data to be presented to the user are determined to not be for the same patient. As another example, the consistency requirement may include a condition that each image be from the same imaging session or exam. That is, the consistency requirement is violated when data claims for each image to be presented to the user are determined to not have been acquired during the same imaging session or exam. As another example, the consistency requirement may require that data from only a defined set of trusted sources is to be displayed. As another example, the consistency requirement may require that only data collected during the past year is to be displayed. As another example, the consistency requirement may require that the data displayed have been collected at a specified hospital.

The consistency requirement may be received by a consistency requirement input component of the validation component, for example. That is, in certain embodiments, the validation component includes a consistency requirement input component adapted to receive a consistency requirement.

At step 320, a data claim is received. The data claim is associated with clinical data to be presented to a user. The data claim may be similar to the data claims discussed above, for example. One or more data claims may be received.

A data claim is associated with clinical data. The clinical data may be presented to a user. A data claim is metadata that makes "claims" about the associated clinical data. That is, each data claim is treated as an assertion that the value of the claim is correct. For example, a data claim called "creation date" may include a value of "Nov. 14, 2006." This data claim is treated as an assertion that the creation date of the associated clinical data is Nov. 14, 2006. In certain embodiments, a data claim is implemented as a set of (name, value) pairs. The data claims are stored as (name, value) pairs to maximize flexibility, however, other formats may be used.

In certain embodiments, a set of "well-known" fields with predefined names are provided that a compliant system supports. This may allow a base-level of interoperability. For example, these fields may include patient identifiers, exam identifiers, MRNs, creation dates, modification dates, and source of the clinical data. In addition, in certain embodiments, systems may be customized to define their own fields, which will then support interoperation amongst only those applications for those fields.

A set of claims is referred to as a data claims block. A data claims block includes one or more data claims. In addition, the data claims block may include a digital signature. Alternatively, the data claim itself may include a digital signature. The digital signature may be used to verify the data claims and/or the clinical data. In certain embodiments, the digital signature is generated from one or more data claims in the data claims block. In certain embodiments, the digital signature is generated from the data claims and the clinical data. For example, the digital signature may allow a system or user to verify that the data has not been tampered with. As another example, the digital signature may allow a system or user to verify that the metadata came from the specified validation authority using standard cryptographic techniques.

The data claim may be received by a validation component similar to the validation component 110 and/or the validation component 210, discussed above, for example. For example, the validation component may receive a data claim from an application. For example, the validation component may receive multiple data claims from a single application. As another example, the validation component may receive multiple data claims from different applications.

The data claim may be received through an API similar to the API 115 and/or the metadata API 215, for example. The data claim may be received by a data claim input component of the validation component, for example. That is, in certain embodiments, the validation component includes a data claim input component adapted to receive a data claim.

At step 330, a data claim is verified. The data claim may be the data claim received at step 320, discussed above, for example.

The data claim may be included in a data claims block. The data claims block may include a digital signature. Alternatively, the data claim itself may include a digital signature. The digital signature may be used to verify the data claims and/or the clinical data. In certain embodiments, the digital signature is generated from one or more data claims in the data claims block. In certain embodiments, the digital signature is generated from the data claims and the clinical data. For example, the digital signature may allow a system or user to verify that the data has not been tampered with. As another example, the digital signature may allow a system or user to verify that the metadata came from the specified validation authority using standard cryptographic techniques. The digital signature may be generated by a validation authority similar to the validation authority 240, discussed above. The validation authority may be the entity that originally generated the data claim and associated it with the clinical data, for example.

The data claim may be verified by a validation component similar to the validation component 110 and/or the validation component 210, discussed above, for example.

In certain embodiments, the data claim may be verified by a validation authority similar to the validation authority 240, discussed above, for example. For example, the validation component may receive a data claims block for clinical data. The validation component may then utilize the validation authority that generated the data claims block (as indicated by a data claim in the data claims block, for example) to verify that the data claims received by the validation component are correct. That is, the validation authority may vouch for the accuracy of the data claims. The validation component may communicate with the validation authority through the metadata API, for example.

At step 340, a data claim is translated. The data claim may be translated by a translation authority similar to the translation authority 250, discussed above, for example.

The data claim may be translated from one namespace to another namespace. Data claims generated by different systems (e.g., validation authorities), may have different namespaces. For example, different hospitals may use different identifiers to identify the same patient. Thus, even though data claims may logically be for the same patient, the data claims themselves may include different values for the patient identifier because the values are from different namespaces.

The validation component may use a translation authority to translate a data claim from the namespace of one system to the namespace of another system, for example. The validation component may communicate with the translation authority through the metadata API, for example.

At step 350, a data claim is evaluated. The data claim may be evaluated by a validation component similar to the validation component 110 and/or the validation component 210, discussed above, for example. The data claim may be evaluated based at least in part on a consistency requirement. The consistency requirement may be the consistency requirement received at step 310, discussed above, for example.

As discussed above, the consistency requirement may specify a variety of different conditions to be met. The consistency requirement may include one or more conditions. If the consistency requirement is not met, a violation is said to occur. For example, the consistency requirement may include criteria that clinical data be for the same patient. That is, the consistency requirement is violated when data claims for each piece of clinical data to be presented to the user are determined to not be for the same patient. As another example, the consistency requirement may include a condition that each image be from the same imaging session or exam. That is, the consistency requirement is violated when data claims for each image to be presented to the user are determined to not have been acquired during the same imaging session or exam. As another example, the consistency requirement may require that data from only a defined set of trusted sources is to be displayed. As another example, the consistency requirement may require that only data collected during the past year is to be displayed. As another example, the consistency requirement may require that the data displayed have been collected at a specified hospital.

At step 360, a user is alerted. The user may be alerted by an alert component similar to the alert component 130, discussed above, for example. The user may be alerted in a variety of ways. For example, an audible or visual alert may be generated, such as a beep or a flashing window. As another example, a pop-up window to signal to the user that inconsistent data is being displayed may be generated.

One or more of the steps of the method 300 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Certain embodiments of the present invention provide improved patient safety through guaranteed data consistency. Certain embodiments of the present invention provide a standard mechanism for guaranteed validity and traceability of clinical data. Thus, certain embodiments of the present invention provide systems and methods for clinical data validation. In addition, certain embodiments provide a technical effect of improved patient safety through guaranteed data consistency. Certain embodiments provide a standard mechanism for guaranteed validity and traceability of clinical data. Thus, certain embodiments provide a technical effect of clinical data validation.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for validating clinical data to be displayed to a user, the method including:
receiving a consistency requirement specifying whether clinical data retrieved for presentation to a user is intended to be displayed;
receiving a first data claim associated with first clinical data and a second data claim associated with second clinical data, the first clinical data retrieved from a first data source for presentation to a user, the second clinical data retrieved from a second data source for presentation to the user, the first data claim comprising metadata regarding the retrieved first clinical data to be displayed, the second data claim comprising metadata regarding the retrieved second clinical data to be displayed, wherein the first data claim is received from a first application in a first namespace and the second data claim is received from a second application in a second namespace;
translating, via a processor, the second clinical data to the first namespace;
evaluating, via the processor, the first data claim and the second data claim based at least in part on the consistency requirement;
in response to evaluating the first data claim and the second data claim, determining if the retrieved first clinical data to be displayed or the retrieved second clinical data to be displayed violates the consistency requirement;
in response to displaying the retrieved first clinical data, providing an alert to the user if the displayed first clinical data violates the consistency requirement, and not providing the alert to the user if the displayed first clinical data does not violate the consistency requirement;
in response to displaying the retrieved second clinical data, providing the alert to the user if the displayed second clinical data violates the consistency requirement, and not providing the alert to the user if the displayed second clinical data does not violate the consistency requirement; and
when the alert is provided to the user, re-evaluating the corresponding data claim in response to a change in the displayed clinical data.

2. The method of claim 1, wherein the consistency requirement specifies that the first clinical data be for a specific patient.

3. The method of claim 1, wherein the consistency requirement specifies that the first clinical data be for a specific exam.

4. The method of claim 1, wherein the first clinical data includes a medical image associated with a patient, the medical image acquired from an imaging modality.

5. The method of claim 1, wherein the first clinical data includes an electronic medical record associated with a patient.

6. The method of claim 1, further including verifying the first data claim based at least in part on a digital signature, said verification including at least one of: verifying the first data claim has not been tampered with or verifying the first data claim came from a specified validating authority.

7. The method of claim 1, further including verifying the first data claim with a validation authority that generated the first data claim to verify that the first data claim is correct.

8. The method of claim 1, further including translating the first data claim with a translation authority.

9. The method of claim 1, wherein the consistency requirement specifies that the first clinical data be collected during the past year.

10. The method of claim 1, wherein the consistency requirement specifies that the first clinical data be collected at a specific hospital.

11. The method of claim 1, wherein at least the first application is different than the second application or the first namespace is different than the second namespace.

12. A clinical data validation system for validating clinical data to be displayed to a user, the system including:
a consistency requirement input component operatively connected to a processor, the consistency requirement input component to receive a consistency requirement specifying whether clinical data retrieved for presentation to a user is intended to be displayed;
a data claim input component operatively connected to the processor, the data claim input component to:

receive a first data claim associated with first clinical data, the first clinical data retrieved from a first data source for presentation to a user, the first data claim comprising metadata regarding the retrieved first clinical data to be displayed, wherein the first data claim is received from a first application in a first namespace; and receive a second data claim associated with second clinical data, the second clinical data retrieved from a second data source for presentation to the user, the second data claim comprising metadata regarding the retrieved second clinical data to be displayed, wherein the second data claim is received from a second application in a second namespace;

a validation component operatively connected to the processor, the validation component to use the processor to:

translate the second data claim to the first namespace; and evaluate the first data claim and the second data claim based at least in part on the consistency requirement to determine if the retrieved first clinical data to be displayed or the retrieved second clinical data to be displayed violates the consistency requirement; and an alert component operatively connected to the processor, the alert component to, after the retrieved first clinical data and the retrieved second clinical data are displayed:

provide an alert to the user if the displayed first clinical data violates the consistency requirement, and not provide an alert to the user if the displayed first clinical data does not violate the consistency requirement; and provide the alert to the user if the displayed second clinical data violates the consistency requirement, and not provide the alert to the user if the displayed second clinical data does not violate the consistency requirement, and wherein when the alert is provided to the user, the validation component is to re-evaluate the corresponding data claim in response to a change in the displayed clinical data.

13. The system of claim 12, further including a translation authority to translate a data claim from one namespace to another namespace.

14. The system of claim 12, further including a validation authority that generated the first data claim, the validation authority to verify that the first data claim is correct.

15. The system of claim 12, wherein the first data claim is included in a data claims envelope.

16. The system of claim 12, further including a standardized application programming interface (API) for accessing at least the first data claim or the second data claim.

17. The system of claim 12, wherein at least the first application is different than the second application or the first namespace is different than the second namespace.

18. A non-transitory computer-readable medium including a set of instructions for execution on a computer, the set of instructions, when executed, to cause the computer to at least:

receive a consistency requirement that specifies whether clinical data retrieved for presentation to a user is intended to be displayed;

receive a first data claim associated with first clinical data, the first clinical data retrieved from a first data source for presentation to a user, the first data claim comprising metadata regarding the retrieved first clinical data to be displayed, wherein the first data claim is received from a first application in a first namespace;

receive a second data claim associated with second clinical data, the second clinical data retrieved from a second data source for presentation to the user, the second data claim comprising metadata regarding the retrieved second clinical data to be displayed, wherein the second data claim is received from a second application in a second namespace;

translate the second data claim to the first namespace;

evaluate the first data claim and the second data claim based at least in part on the consistency requirement;

in response to evaluation of the first data claim and the second data claim, determine if the retrieved first clinical data to be displayed or the second clinical data to be displayed violates the consistency requirement;

display the retrieved first clinical data and the retrieved second clinical data;

after the retrieved first clinical data is displayed, provide an alert to the user if the displayed first clinical data violates the consistency requirement, and not provide the alert to the user if the displayed first clinical data does not violate the consistency requirement;

after the retrieved second clinical data is displayed, provide the alert to the user if the displayed second clinical data violates the consistency requirement, and not provide the alert to the user if the displayed second clinical data does not violate the consistency requirement; and when the alert is provided to the user, re-evaluate the corresponding data claim in response to a change in the displayed clinical data.

19. The non-transitory computer-readable medium of claim 18, wherein at least the first application is different than the second application or the first namespace is different than the second namespace.

* * * * *